United States Patent [19]

Asato et al.

[11] Patent Number: 4,886,830

[45] Date of Patent: Dec. 12, 1989

[54] MONO- AND DIEPOXIDE DERIVATIVES OF 23-DEOXYL-LL-F28249 COMPOUNDS

[75] Inventors: Goro Asato, Titusville; Susan Y. Tamura, Hamilton Square, both of N.J.

[73] Assignee: American Cyanamid Company, Stamford, Conn.

[21] Appl. No.: 22,847

[22] Filed: Mar. 6, 1987

[51] Int. Cl.$^4$ .................. A61K 31/335; C07D 311/96
[52] U.S. Cl. ....................................... 514/450; 549/264
[58] Field of Search ......................... 549/264; 514/450

[56] References Cited

U.S. PATENT DOCUMENTS 4,530,921  7/1985  Mrozik ................................. 549/264
4,696,922  9/1987  Sturm et al. ......................... 549/264

FOREIGN PATENT DOCUMENTS 170006    2/1986  European Pat. Off. .
2166436A  5/1986  United Kingdom .
2176182A 12/1986  United Kingdom ................. 549/264

OTHER PUBLICATIONS

Abstract of J.A. 84/036,681.

Primary Examiner—Glennon H. Hollrah
Assistant Examiner—Ba Trinh
Attorney, Agent, or Firm—Estelle J. Tsevdos

[57] ABSTRACT

The present invention relates to novel derivatives of LL-F28249 compounds wherein the 23-hydroxyl group is replaced with hydrogen and the double bond at the C(26,27)-position is epoxidized concomitant with or without epoxidation of the double bond at the C(14,15)-position. The LL-F28249 compounds (collectively) are isolates from the fermentation broth of *Streptomyces cyaneogriseus* subspecies noncyanogenus having deposit accession number NRRL 15773. The compounds of the present invention are derived by regioselective epoxidation of 5,23-O,O-bissilylated LL-F28249 compounds at low temperature, desilylation, re-silylation of the 5-hydroxyl group, thiocarbonylation of the 23-hydroxyl group, disilyation followed by tributyltin hydride reduction. The novel deoxy compounds of the present invention have anthelmintic, insecticidal, ectoparasiticidal, nematicidal and acaricidal activity. Compositions containing these described derivatives as active ingredients thereof are described herein.

9 Claims, No Drawings

MONO- AND DIEPOXIDE DERIVATIVES OF 23-DEOXYL-LL-F28249 COMPOUNDS

BACKGROUND OF THE INVENTION

The present invention relates to novel mono- and diepoxide derivatives of 23-deoxy LL-F28249 compounds. The term LL-F28249 is used to describe compounds produced by the fermentation broth of *Streptomyces cyaneogriseus* subspecies noncyanogenus deposited in the NRRL under deposit accession No. 15773. The morphological characteristics, compounds and method for their production are disclosed in European Patent Application No. 170,006, incorporated herein by reference thereto.

The LL-F28249 compounds are complex macrolids which have 5 olefinic bonds. The regioselective epoxidation of the C(26,27)-olefinic bond concomitant with or without epoxidation of the C(14,15)-olefinic bond, followed by replacing the hydroxyl group at the 23-position with hydrogen is the subject of the present invention. These mono- and diepoxy-23-deoxy-LL-F28249 compounds are useful for the prevention, treatment or control of helmintic, ectoparasitic, insect, acarid, and nematode infections and infestations in warm-blooded animals and agricultural crops.

SUMMARY OF THE INVENTION

The present invention provides novel C(26,27)epoxide and C(14,15;26,27)-diepoxide-23-deoxy derivatives of the compounds designated LL-F28249α, β, ε, ζ, θ and ι.

The LL-F28249 compounds have the following structural formula:

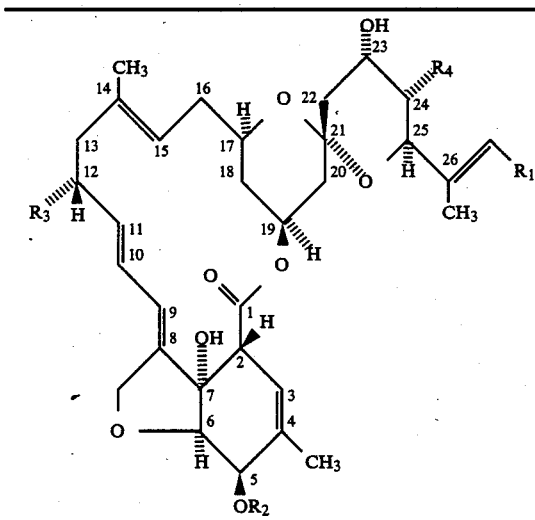

| Component | $R_1$ | $R_2$ | $R_3$ | $R_4$ |
|---|---|---|---|---|
| LL-F28249α | CH(CH₃)₂ | H | CH₃ | CH₃ |
| LL-F28249β | CH₃ | H | CH₃ | CH₃ |
| LL-F28249ε | CH(CH₃)₂ | H | H | CH₃ |
| LL-F28249ζ | CH₂CH₃ | H | CH₃ | CH₃ |
| LL-F28249θ | CH(CH₃)₂ | H | CH₃ | CH₂CH₃ |
| LL-F28249ι | CH(CH₃)₂ | H | CH₂CH₃ | CH₃ |

The compounds of the present invention are useful anthelmintics, ectoparasiticides, insecticides, acaricides and nematicides in treating, preventing or controlling such diseases in warm-blooded animals, such as poultry, cattle, sheep, swine, rabbits, horses, dogs, cats and human beings and agricultural crops.

Although these diseases have been recognized for years and therapies exist for the treatment and prevention of the diseases, the present invention provides novel compounds in the search for more effective therapy useful in the treatment of said diseases. For instance, U.S. application for Letters Pat. Ser. Nos. 907,283, 907,188, 907,281, 907,259, 907,187 and 907,284 of Asato and Asato et al., filed on September 12, 1986 and incorporated herein by reference thereof provide compounds for such treatments. Also U.S. application for Letters Pat. Ser. Nos. 022849, 022850, 022906, 022848, and 022846 of Asato et al., filed concurrently herewith and incorporated herein by reference thereof provide compounds for such treatments.

U.S. Pat. No. 3,950,360, Aoki et al., April 13, 1976 discloses certain antibiotic substances obtained by culturing a Streptomyces microorganism, said compounds being useful as insecticides and acaricides. Further, an entire series of U.S. patents relates to certain compounds produced by the fermentation of *Streptomyces avermitilis* (U.S. Pat. No. 4,171,314, Chabala et al., October 16, 1979; U.S. Pat. No. 4,199,569, Chabala et al., April 22, 1980; U.S. Pat. No. 4,206,205, Mrozik et al., June 3, 1980; U.S. Pat. No. 4,310,519, Albers-Schonberg, January 12, 1982; U.S. Pat. No. 4,333,925, Buhs et al., June 8, 1982). U.S. Pat. No. 4,423,209, Mrozik, December 27, 1983 relates to the process of converting some of these less desirable components to more preferred ones. Finally, British Patent Application No. 2166436 A discloses antibiotics also, as does Belgium Patent Application No. 9041709A.

The present compounds or the pharmaceutically and pharmacologically acceptable salts thereof exhibit excellent and effective treatment, prevention and/or control of these serious diseases of warm-blooded animals.

It is an object of the present invention, therefore, to provide novel C(26,27)-epoxide and C(14,25;26,27)-diepoxide-23-deoxy derivatives of LL-F28249α, β, ε, ζ, θ and ι. It is a further object of the present invention to provide a process for the preparation of these derivatives and to provide methods for preventing, treating or controlling endo- and ectoparasitic (collectively parasitic), insect, nematode, and acarid infections and infestations in warm-blooded animals and agricultural crops by providing compositions containing prophylactically, therapeutically, pharmaceutically or pesticidally effective amounts of the novel compounds. Another object of the invention is to provide compounds useful as intermediates for the preparation of novel antiparasitic and insecticidal compounds.

These and other objects of the invention will become apparent by the more detailed description of the invention provided hereinbelow.

DETAILED DESCRIPTION OF THE INVENTION

The LL-F28249 compounds which may act as precursors of the present compounds are represented by the following structural formula,

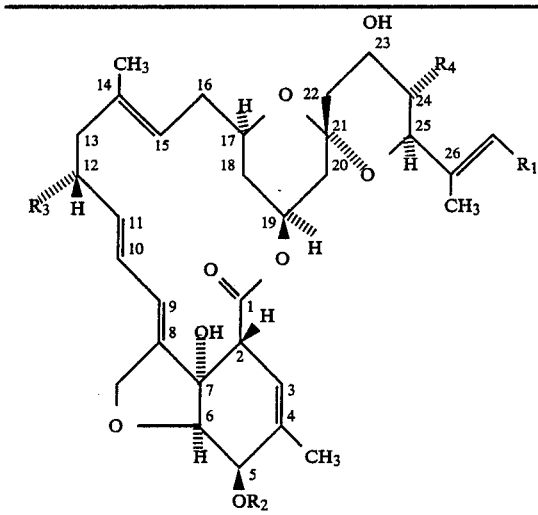

| Component | $R_1$ | $R_2$ | $R_3$ | $R_4$ |
|---|---|---|---|---|
| LL-F28249α | CH(CH₃)₂ | H | CH₃ | CH₃ |
| LL-F28249β | CH₃ | H | CH₃ | CH₃ |
| LL-F28249ε | CH(CH₃)₂ | H | H | CH₃ |
| LL-F28249ζ | CH₂CH₃ | H | CH₃ | CH₃ |
| LL-F28249θ | CH(CH₃)₂ | H | CH₃ | CH₂CH₃ |
| LL-F28249ι | CH(CH₃)₂ | H | CH₂CH₃ | CH₃ |

The compounds of the instant invention are represented by the following structural formula:

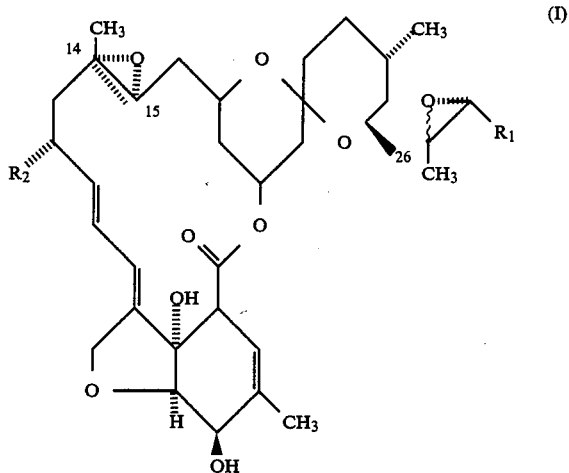

(I)

wherein $R_1$ is methyl or isopropyl; $R_2$ is hydrogen, methyl or ethyl; and the dotted triangular figure with oxygen at C(14,15) indicates that either a double bond or an epoxide is present.

A preferred group of compounds of structure (I) includes $R_1$ as isopropyl; $R_2$ as methyl; and the dotted triangular figure with oxygen at C(14,15) indicating that either a double bond or an epoxide is present.

The most preferred compound of structure (I) include $R_1$ as isopropyl; $R_2$ as methyl; and the dotted triangular figure with oxygen at C(14,15) indicating that a double bond is present.

The monoepoxide and diepoxide compounds of the present invention are prepared by treating the appropriately-protected LL-F28249 compound with a mild oxidizing agent at temperatures less than −20° C. The oxidizing agent useful in the present invention is capable of selectively oxidizing the C(26,27) double as well as the C(14,15) double bond, but not other double bonds in the molecule. Selectivity also is attained by controlling the temperature of the oxidation in an inert solvent, such as methylene chloride, chloroform and the like. Peroxide oxidizing agents, such as m-chloroperoxybenzoic acid, are representative of the preferred oxidants in preparing the monoepoxy and diepoxy compounds of the present invention.

Generally, a slight excess of the oxidizing agent is employed, such as 5%–20% excess, when it is desired to prepare the C(26,27) epoxide in good yield. When epoxidation at the C(14,15) double bond also is desired, an amount of oxidizing agent equivalent to a slight excess of 2 moles is employed.

The epoxidation is generally conducted at temperatures less than −20° C. and −78° C. and is complete in 3–6 hours. Separation of the monoepoxide and the diepoxide is readily achieved by standard chromatographic techniques, such as column or preparative-plate chromatography.

The starting compounds of the present invention include the above-mentioned LL-F28249 fermentation products. These compounds are initially derivatized at the 5- and 23-hydroxy groups with a trisubstituted alkyl silyl group. One of the preferred protecting group is t-butyldimethylsilyl group. The reaction is carried out by allowing the LL-F28249 compound to react with at least two molar equivalents of a substituted silyl halide, preferably a silyl chloride in an aprotic solvent such as dimethylformamide, methylene chloride or ethylene dichloride in the presence of imidazole and/or 4-dimethylaminopyridine. The reaction is completed in 2–8 hours at 50° C. to 80° C.

The silyl group is removed after epoxidation by stirring the silyl derivative in methanol containing an acid, such as p-toluenesulfonic acid monohydrate or acetic acid. The reaction is complete in 1 to 8 hours at 0° C. to 25° C., preferably at 0° C. to 10° C. Desilylation also may be conducted in aqueous acetic acid at room temperature. The addition of a catalytic amount of $FeCl_3$ in the desilylation especially facilitates the desilylation.

In preparing the compounds of the present invention, the 5-hydroxy group is protected following the epoxidation. Suitable protecting groups are trisubstituted silyl groups, such as t-butyldimethylsilyl and trimethylsilyl, or trisubstituted silyloxyacetyl groups, such as t-butyldimethylsilyloxy acetyl group. The protecting groups, however, are not limited to these groups since other useful protecting groups such as acyl and substituted acyl, such as acetyl, trifluoroacetyl, chloroacetyl, trichloroacetyl, phenoxyacetyl and the like, also are useful in the process of the present invention.

One of the preferred protecting groups is t-butyldimethylsilyl. This group is attached to the 5-hydroxyl group by reacting an unprotected 5-hydroxy C(26,27)-epoxy- or C(14,15;26,27)-diepoxy-LL-F28249 compound with t-butyldimethylsilyl chloride in the presence of a base, such as imidazole, pyridine, 4-dimethylaminopyridine, triethylamine and the like, in an aprotic solvent such as methylene chloride, toluene, ethylacetate, tetrahydrofuran, ethylenedichloride and the like. The reaction is stirred at a temperature of about 0° C. to 30° C., and the reaction is complete in several hours, depending on the temperature of the reaction. The completion of the reaction is usually monitored by high performance liquid chromatography (HPLC) using reverse phase on a Whatman Partisil CCS/C$_8$ rapid analysis column.

Another preferred protecting group is t-butyldimethylsilyloxy acetyl group. This group is attached to the 5-hydroxyl group by combining the unprotected C(26,27)-epoxy- or C(14,15;26,27)-diepoxy-LL-F28249 compound in an aprotic solvent such as methylene chloride, toluene, ethyl acetate, tetrahydrofuran, ethylenedichloride and the like, containing a tertiary amine, such as pyridine or triethylamine, and adding the protecting agent in the form of an acid halide. The reaction is conducted at a temperature of about 0° C. to 30° C. and is monitored by HPLC for completion.

For instance, the reaction of the present invention is carried out by allowing the C(26,27)-epoxy or C(14,15;26,27)-diepoxy-LL-F28249 compound to react with a molar equivalent or slight excess of the trisubstituted silyl chloride in the presence of imidazole with or without a catalytic amount of 4-dimethylaminopyridine. The reaction is conducted in an inert solvent, such as methylene chloride, ethylene dichloride or dimethylformamide at 15° C.–30° C. This protected epoxy or diepoxy compound is then reacted with O-(4-methylphenyl)chlorothiolformate in pyridine containing 4-dimethylaminopyridine at a temperatures of 25° C. to 50° C. The resulting 23-O[(4-methylphenoxy)thiocarbonyl] derivative is desilylated with acid as described hereinabove and then is reduced in an inert solvent, such as refluxing toluene, under nitrogen atmosphere with tributyltin hydride/azobisisobutyronitrile until the reaction is complete. The reduced product is the mono- or diepoxide derivatives, 23-deoxy-LL-F28249 compound.

The process is schematically shown in the following diagram:

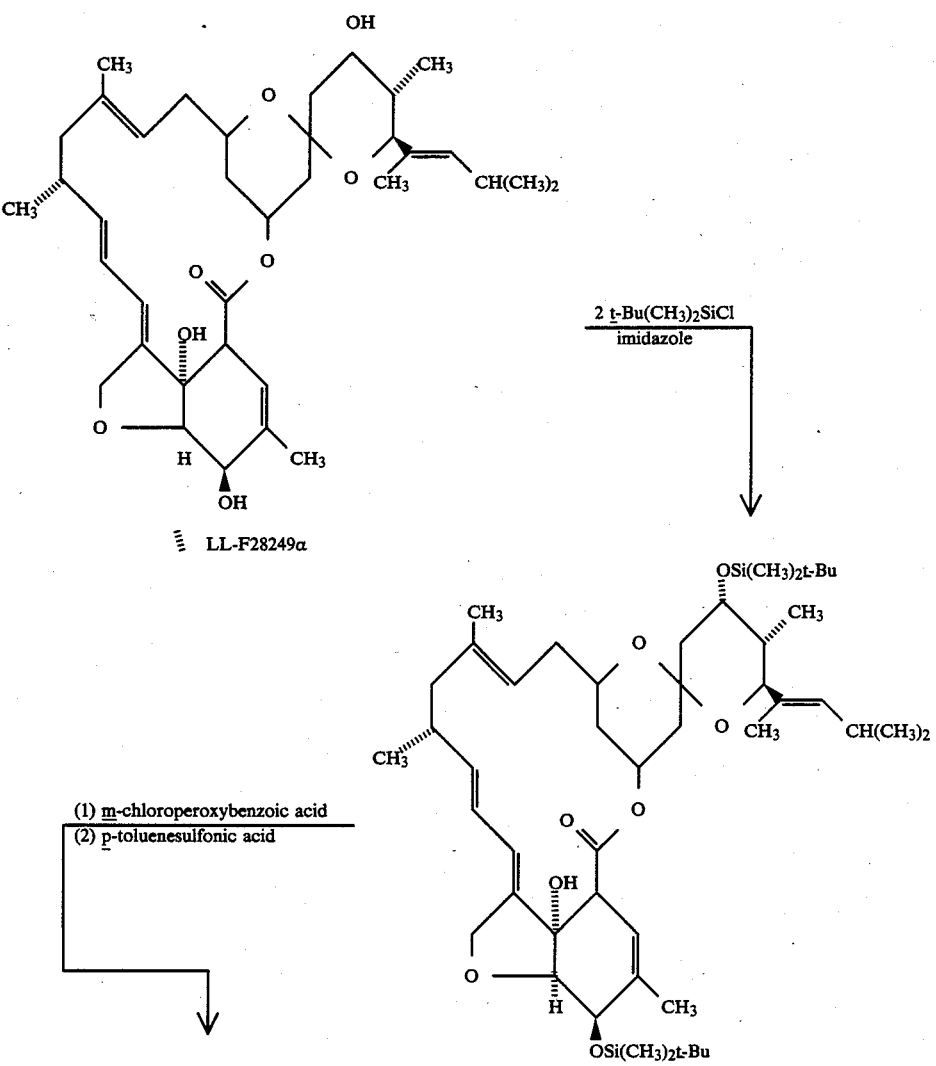

-continued
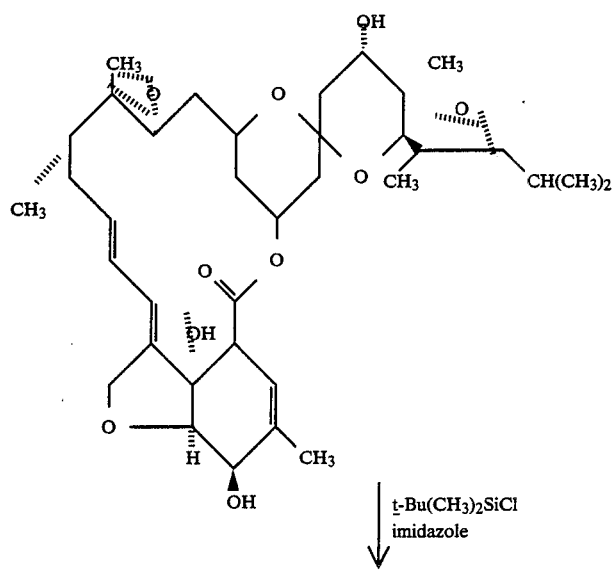
↓ t-Bu(CH₃)₂SiCl
  imidazole
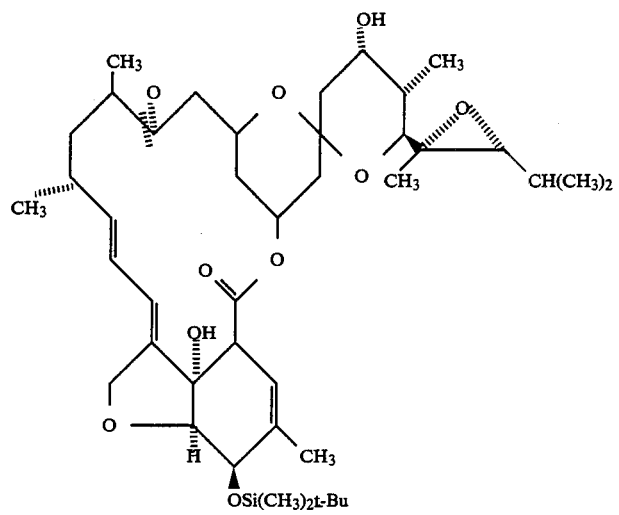
$$\underset{\|}{S}$$
(1) 4.CH₃C₆H₄OCCl/Pyridine/DMAP
(2) p-Toluenesulfonic acid/MeOH
↓
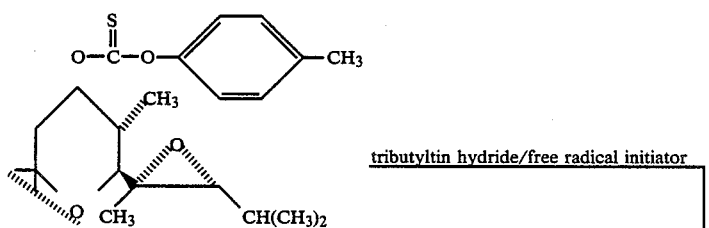
Partial structural
tributyltin hydride/free radical initiator ⟶ ↓

-continued

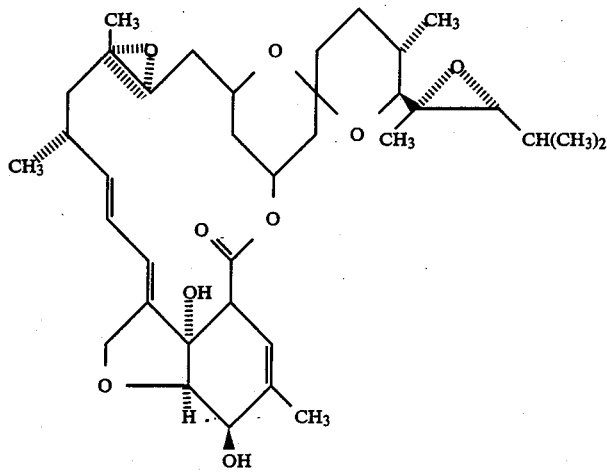

The novel compounds of the present invention have significant activity as anthelmintics, ectoparasiticides, insecticides, nematicides and acaricides in human and animal health areas and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum primarily attack the intestinal tract while others, such as Haemonchus and Ostertagis, are most prevalent in the stomach. Still others such as Dictyocaulus are found in the lungs. Also, other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs, and if left untreated, may result in death of the infected host. The mono- and diepoxides of the 23-deoxy-LL-F28249 derivatives of the LL-F28249 compounds of the present invention unexpectedly have high activity against these parasites.

Additionally, they also are active against Dirofilaria in dogs, Nematospiroides, Syphacia, Aspiculuris in rodents, arthropod ectoparasites such as ticks, mites, lice, fleas, blowfly of animals and birds, the ectoparasite Lucilia sp. of sheep, biting insects and migrating dipterous larvae such as Hypoderma sp. in cattle, Gastrophilus in horses and Cuterebra sp. in rodents.

The compounds of the present invention also are useful in treating, preventing or controlling parasites which infect human beings, as well. The most common genera of parasites of the gastrointestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra-intestinal stages of the intestinal worms Strongyloides and Trichinella. The present compounds also are of value against arthropods parasitizing man, biting insects and other dipterous pests causing annoyance to man.

These compounds are also active against household pests such as the cockroach, Blattella sp., clothes moth, Tineola sp., carpet beetle, Attagenus sp., and the housefly Musca domestica.

Insects pests of stored grains such as Tribolium sp., Tenebrio sp., and of agricultural plants such as spider mites (Tetranychus sp.), southern army worms, tobacco budworms, boll weevils, aphids (Acyrthiosiphon sp.), migratory orthopterans such as locusts and immature stages of insects living on plant tissues are controlled by the compounds of the present invention as well as soil nematodes and plant parasites such as Meloidogyne sp., which may be of importance in agriculture.

The compounds of the present invention may be administered orally or parenterally for animal and human usage, and may be formulated in liquid or solid form for agricultural use. Oral administration may take the form of a unit dosage from such as a capsule, bolus or tablet, or as a liquid drench where used as an anthelmintic for animals.

The animal drench is normally a solution, suspension or dispersion of the active compound, usually in water, together with a suspending agent such as bentonite and a wetting agent or like excipient. Generally, the drenches also contain an antifoaming agent. Drench formulations generally contain about 0.001% to 0.5%, by weight, of the active compound. Preferred drench formulations contain about 0.01% to 0.1% by weight.

Capsules and boluses comprise the active ingredient admixed with a carrier vehicle such as starch, talc, magnesium stearate or di-calcium phosphate.

Where it is desired to administer these derivatives of LL-F28249 in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the active compound depending upon factors such as the type of infection and the weight of the host.

When the active compound is to be administered via an animal feedstuff, it is intimately dispersed in the feed or used as a top dressing or in the form of pellets which may then be added to the finished feed or optionally fed separately. Alternatively, the active compounds of the present invention may be administered to animals parenterally, such as by intraruminal, intramuscular, intratracheal, or subcutaneous injection. In such an event, the active compound is dissolved or dispersed in a liquid carrier vehicle.

For parenteral administration, the active compound is suitably admixed with an acceptable vehicle, preferably of the vegetable oil variety such as peanut oil, cotton seed oil and the like. Other parenteral vehicles such as organic preparations using solketal, propylene glycol, glycerol formal, and aqueous parenteral formulation also are used. The active 23-deoxy compound or compounds of the present invention are dissolved or suspended in the parenteral formulation for administration. Such formulations generally contain about 0.005%, by weight, of the active compound.

Although the compounds of the present invention are primarily used in the treatment, prevention or control of helminthiasis, they also are useful in the prevention and treatment of diseases caused by other parasites. For example, arthropod parasites such as ticks, lice, fleas, mites and other biting insects in domesticated animals and poultry are controlled by the present compounds. These compounds also are effective in treatment of parasitic diseases that occur in other animals including human beings. The optimum amount to be employed will, of course, depend upon the particular compound employed, the species of animal to be treated and the type and severity of parasitic infection or infestation. Generally, the amount useful in oral administration of these novel compounds is about 0.001 mg to 10 mg per kg of animal body weight, such total dose being given at one time or in divided doses over a relatively short period of time (1–5 days). The preferred compounds of the invention give excellent control of such parasites in animals by administering about 0.025 mg to 3 mg per kg of animal body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the animal's feed, or dissolved or suspended in the drinking water, compositions are provided in which the active compound or compounds are intimately dispersed in an inert carrier or diluent. An inert carrier is one that will not react with the active component and that will be administered safely to animals. Preferably, a carrier for feed administration is one that is, or may be, an ingredient of the animal ration.

Suitable compositions include feed premixes or supplements in which the active compound is present in relatively large amounts, wherein said feed premixes or supplements are suitable for direct feeding to the animal or for addition to the feed either directly or after an intermediate dilution or blending step.

Typical carriers or diluents suitable for such compositions include distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing about 0.005% to 2.0%, by weight, of the active compound are particularly suitable as feed premixes.

Feed supplements, which are fed directly to the animal, contain about 0.0002% to 0.3%, by weight, of the active compounds. Such supplements are added to the animal feed in an amount to give the finished feed the concentration of active compound desired for the treatment, prevention and/or control of parasitic diseases. Although the desired concentration of active compound will vary depending upon the factors previously mentioned as well as upon the particular derivative employed, the compounds of this invention are usually fed at concentrations of about 0.00001% to 0.02% in the feed in order to achieve the desired antiparasitic result.

The compounds also may be administered by pouring on the skin of animals via a solution. Generally, the active compounds are dissolved in a suitable inert solvent, such as dimethylsulfoxide, propylene glycol or the like, alternatively in combination of solvents, for the pour-on administration.

The compounds of this invention also are useful in combating agricultural pests that inflict damage upon growing or stored crops. The present compounds are applied, using known techniques such as sprays, dusts, emulsions and the like, to the growing or stored crops to effect protection from such agricultural pests.

The present invention is illustrated by the following examples which are illustrative of said invention and not limitative thereof.

EXAMPLE 1

5,23-O,O-(Bis-tert-butyldimethylsilyl)-LL-F28249α

In 20 mL of dimethylformamide, 2.0 g of LL-F28249α, 3.72 g of t-butyldimethylsilyl chloride and 2.38 g of imidazole are heated at 60° C. in an oil bath under $N_2$ for 6 hours. The mixture is cooled, quenched with 5 mL of $H_2O$, and diluted with 100 mL of $H_2O$ and 50 mL of brine. The product is then extracted from the aqueous mixture with 2×50 mL of $Et_2O$. The combined $Et_2O$ extracts are washed with 2×25 mL of $H_2O$, 10 mL of brine and dried over $MgSO_4$. Removal of $Et_2O$ affords the title compound which is identified by mass spectrometry and NMR spectroscopy.

EXAMPLES 2 AND 3

LL-F28249α-C(26,27)-Epoxide and LL-F28249α-C(14,15;26,27)-Diepoxide

In 5 mL of $CH_2Cl_2$, 105.4 mg of 5,23-O,O-(bis-t-butyldimethylsilyl)-LL-F28249α is dissolved, and the solution is cooled in dry-ice/acetone bath while 27.8 mg of m-chloroperoxybenzoic acid in 300 mL is added. After an hour of stirring under $N_2$, the temperature is raised to −42° C. for 2 hours and −20° C. for an hour. The solution is washed with 1 mL of saturated $Na_2SO_3$ solution, 1 mL of saturated $NaHCO_3$ solution and 1 mL of brine. After drying over $Na_2SO_4$, the solution is evaporated and residue is chromatographed on silica gel in a flash-chromatography apparatus using 5% EtOAc/hexane followed by 10% EtOAc/hexane.

Fractions 16 to 20 afford 45 mg of monoepoxide while fractions 31-36 affords 12.1 mg of diepoxide.

In 1 mL of MeOH, 30.3 mg of epoxide is stirred with 10.2 mg of p-toluenesulfonic acid monohydrate for 7.5 hours under $N_2$. The mixture is diluted with 1 mL of saturated $NaHCO_3$ solution and 5 mL of $H_2O$ and extracted with 3×2 mL of $Et_2O$. The combined $Et_2O$ extracts are washed with brine, dried over $MgSO_4$, filtered and evaporated to dryness. The residue is chromatographed on silica gel using 2% isopropanol/$CH_2Cl_2$ on a flash-chromatography apparatus to afford 9.4 mg of LL-F28249α-C(26,27)-epoxide, which is identified by mass spectrometry and NMR spectroscopy.

Similarly, the diepoxide is treated with p-toluenesulfonic acid to afford deblocked LL-F28249α-C(14,15;26,27)-diepoxide.

EXAMPLES 4-7

5,23-O,O-(Bis-tert-butyldimethylsilyl)-LL-F28249 compounds

Using the procedure of Example 1, the following bis-silylated products are prepared:

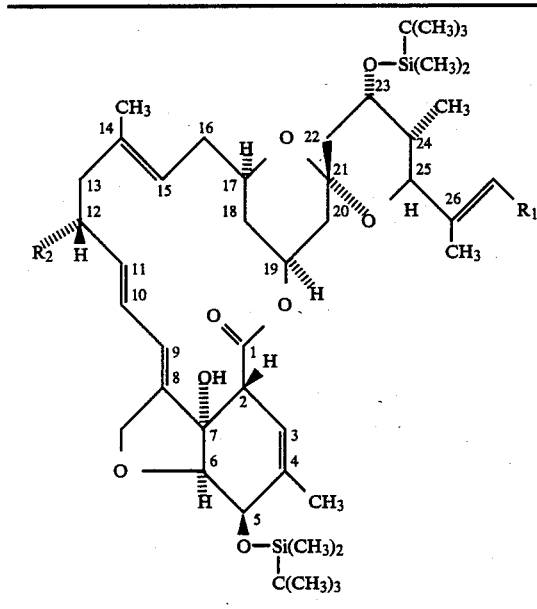

| $R_1$ | $R_2$ |
|---|---|
| $CH(CH_3)_2$ | H |
| $CH_2CH_3$ | $CH_3$ |
| $CH(CH_3)_2$ | $CH_2CH_3$ |
| $CH_3$ | $CH_3$ |

EXAMPLES 8-15

LL-F28249-C(26,27)-epoxides and LL-F28249-C(14,15;26,27)-diepoxides

Using the method of Example 2, the following epoxides and diepoxides of structure (I) are prepared:

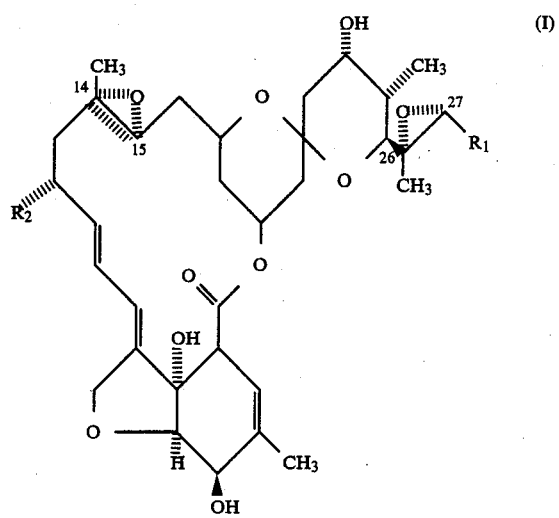

| $R_1$ | $R_2$ |
|---|---|
| $CH(CH_3)_2$ | H |
| $CH_2CH_3$ | $CH_3$ |
| $CH(CH_3)_2$ | $CH_2CH_3$ |
| $CH_3$ | $CH_3$ |

EXAMPLE 16

5-O-tert-Butyldimethylsilyl-LL-F28249α-C(26,27)-epoxide

In 5 mL of $CH_2Cl_2$, 200 mg of LL-F28249α-C(26,27)-epoxide is treated with 130 mg of imidazole and then with 140 mg of t-butyldimethylsilyl chloride (TBDMS chloride) in 5 mL of $CH_2Cl_2$ under $N_2$ at room temperature. The reaction is stirred and monitored by high-performance liquid chromatography (HPLC) for percent conversion. An additional 2.5 equivalents of imidazole and TBDMS chloride are added, and stirring is continued for 5 days. The mixture is then washed with water (2×10 mL) and brine (20 mL), and the $CH_2Cl_2$ solution is dried over $MgSO_4$. The solution is evaporated to dryness and the residue is chromatographed over silica gel using 1:1 heptane/$CH_2Cl_2$ to afford the title compound that is identified by mass spectrometry and NMR spectroscopy.

EXAMPLES 17-20

Using the procedure of Example 16, the following silylated products are prepared:

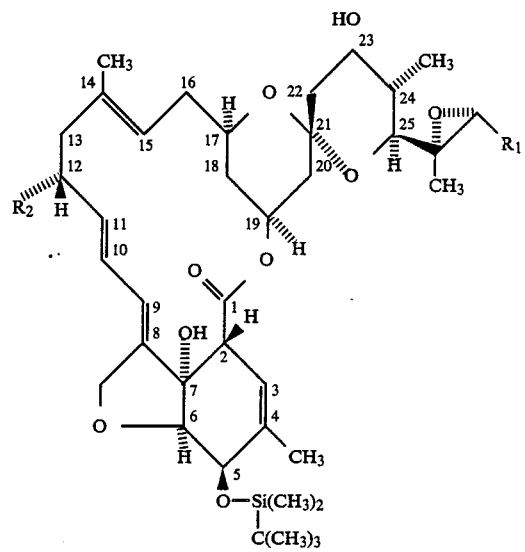

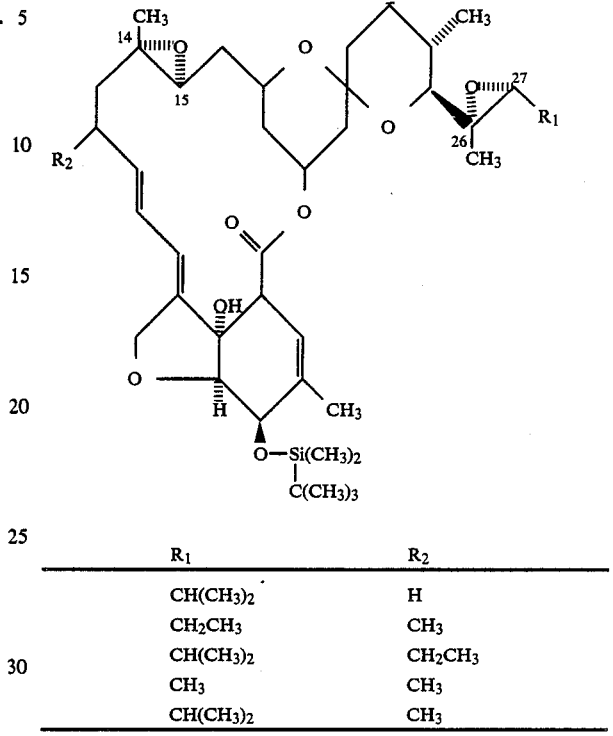

| R₁ | R₂ |
|---|---|
| CH(CH₃)₂ | H |
| CH₂CH₃ | CH₃ |
| CH(CH₃)₂ | CH₂CH₃ |
| CH₃ | CH₃ |
| CH(CH₃)₂ | CH₃ |

EXAMPLE 26

23-O[(4-methylphenoxy)thiocarbonyl]-LL-F28249α-C(26,27)-epoxide

In 2 mL of dry pyridine, 120 mg of 5-O-tert-butyl-dimethylsilyl-LL-F28249α-C(26,27)-epoxide is stirred with 4 mg of 4-dimethylaminopyridine under N₂ in an ice bath, and 0.24 mL of O-p-tolyl chlorothiolformate is added via a syringe. The mixture is stirred at 3° C.–10° C. After 1 hour, 0.2 mL of O-p-tolyl chlorothiolformate is added, and the mixture is stirred at 45° C. for an hour. The mixture is treated with 20 mL of iced H₂O, stirred for 10 minutes and extracted with 3×20 mL of Et₂O. The combined ethereal layers are treated with HOAc and washed successively with H₂O, NaHCO₃ solution and brine. Evaporation of the ether affords the silylated thiocarbonate compound, which is purified by chromatography and identified by mass spectrometry and NMR spectroscopy. Desilylation is then conducted by using the procedure of Example 2 to afford the title compound, that is identified by mass spectrometry and NMR spectroscopy.

EXAMPLES 21–25

Using the method of Example 16, the following silylated diepoxides of structure (I) are prepared:

EXAMPLES 27–30

Using the method of Example 26, the following thiocarbonyl derivatives are prepared:

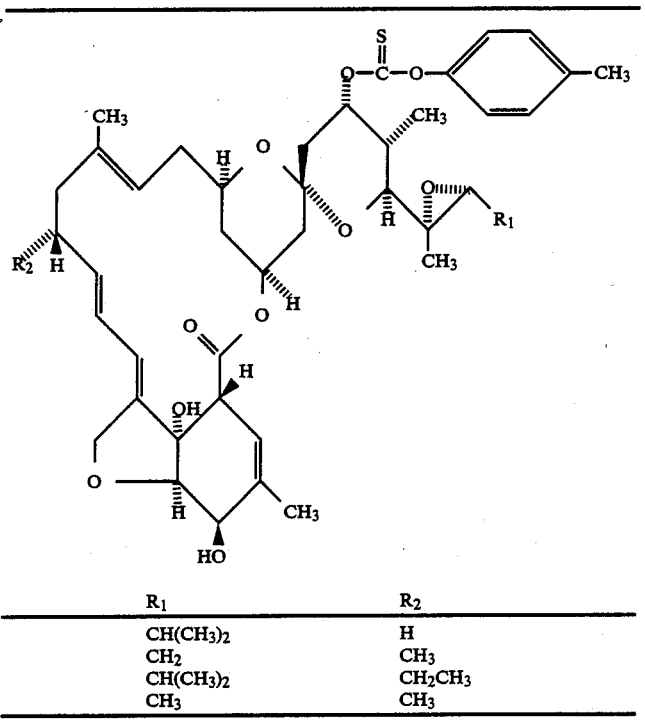

| R₁ | R₂ |
|---|---|
| CH(CH₃)₂ | H |
| CH₂ | CH₃ |
| CH(CH₃)₂ | CH₂CH₃ |
| CH₃ | CH₃ |

EXAMPLES 31-35

Using the procedure of Example 26, the following thiocarbonate derivatives are prepared:

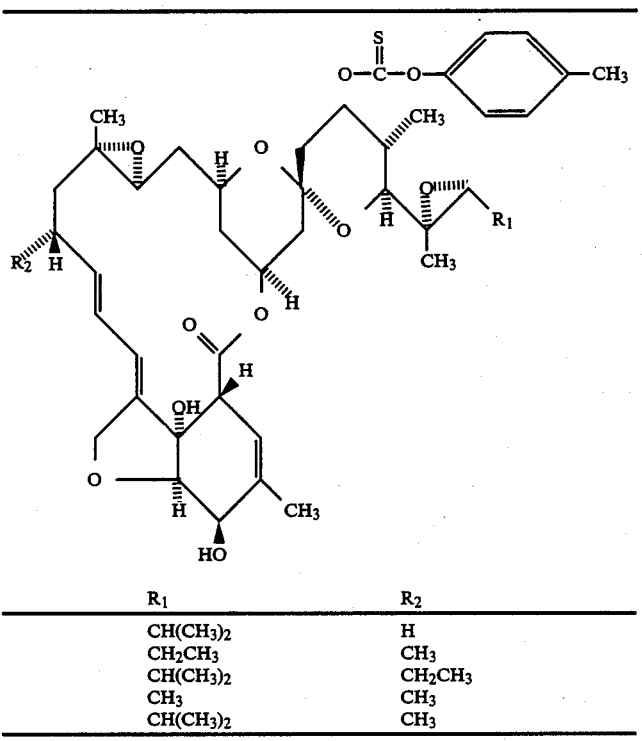

| R₁ | R₂ |
|---|---|
| CH(CH₃)₂ | H |
| CH₂CH₃ | CH₃ |
| CH(CH₃)₂ | CH₂CH₃ |
| CH₃ | CH₃ |
| CH(CH₃)₂ | CH₃ |

EXAMPLE 36

23-Deoxy-LL-F28249α-C(26,27)-Epoxide

In 2 mL of toluene, 6.2 mg of 23-O[(4-methylphenoxy)thiocarbonyl]-LL-F28249α-C(26,27)-epoxide is combined with 3 microliters of tributyltin hydride and a catalytic amount of azobisisobutyronitrile and heated at reflux for 40 minutes. The toluene is removed in vacuo, and the residue is diluted with CH$_2$Cl$_2$ and chromatographed over silica gel using 2% EtOAc in CH$_2$Cl$_2$. The product is monitored by HPLC and evaporation of solvents affords the title compound, that is identified by mass spectrometry and NMR spectroscopy.

EXAMPLES 37-40

Using the procedure of Example 36, the following 23-deoxy-LL-F28249-C(26,27)-epoxides are prepared from their corresponding thiocarbonates listed in Examples 27-30:

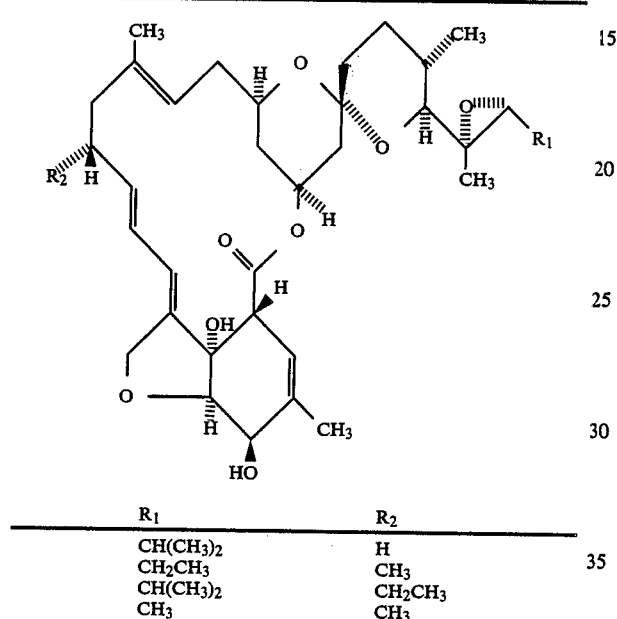

| R$_1$ | R$_2$ |
|---|---|
| CH(CH$_3$)$_2$ | H |
| CH$_2$CH$_3$ | CH$_3$ |
| CH(CH$_3$)$_2$ | CH$_2$CH$_3$ |
| CH$_3$ | CH$_3$ |

EXAMPLES 41-45

Using the procedure of Example 36, the following 23-deoxy-LL-F28249-C(14,15;26,27)-diepoxides are prepared from their corresponding thiocarbonates listed in Examples 31-35:

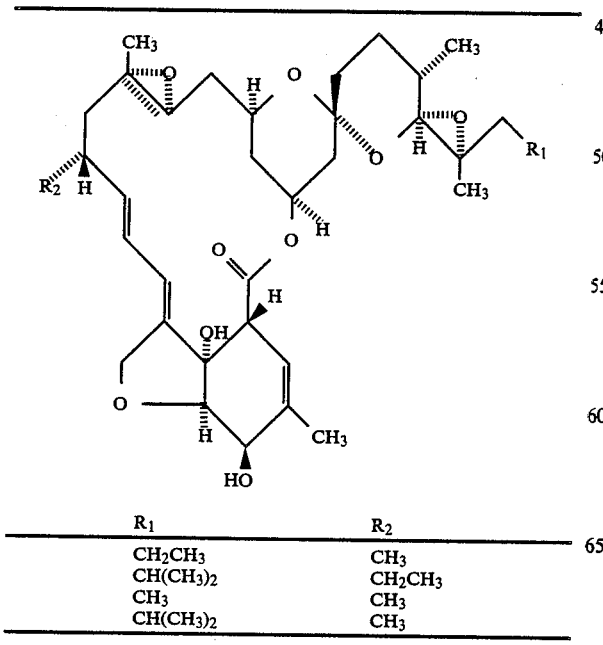

| R$_1$ | R$_2$ |
|---|---|
| CH$_2$CH$_3$ | CH$_3$ |
| CH(CH$_3$)$_2$ | CH$_2$CH$_3$ |
| CH$_3$ | CH$_3$ |
| CH(CH$_3$)$_2$ | CH$_3$ |

What is claimed is:

1. A compound represented by structural formula (I):

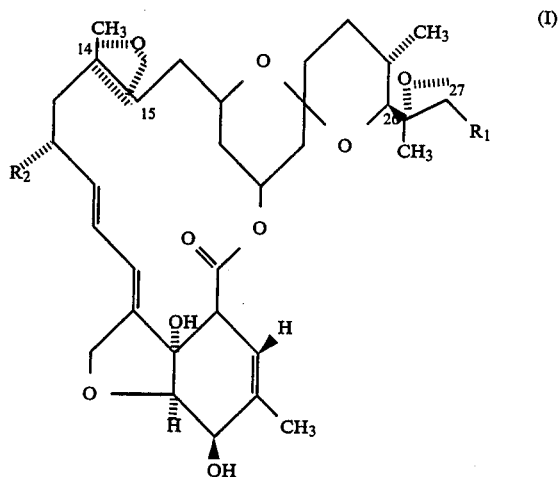

wherein, R$_1$ is methyl or isopropyl; R$_2$ is hydrogen or ethyl; and the dotted triangular figure with oxygen at C(14,15) indicates that either a double bond or an epoxide is present.

2. A compound according to claim 1, wherein R$_1$ is isopropyl; R$_2$ is hydrogen or ethyl; and the dotted triangular figure with oxygen at C(14,15) indicates that either a double bond or an epoxide is present.

3. A compound according to claim 2, wherein R$_1$ is isopropyl; R$_2$ is hydrogen or ethyl; and the dotted triangular figure with oxygen at C(14,15) indicates that a double bond is present.

4. A method for the prevention, treatment or control of endoparasitic or ectoparasitic infections in warm-blooded animals, said method comprising: orally, topically or parenterally administering to an animal infected with endo- or ectoparasites, an endo-or ectoparasiticidally effective amount of a compound represented by structural formula (I),

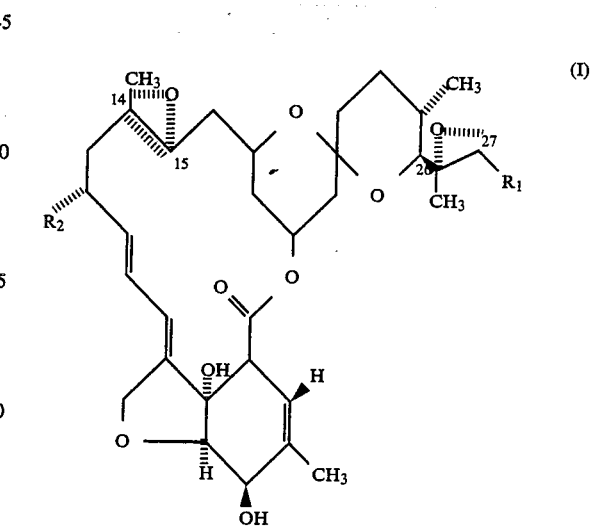

wherein said compound is R$_1$ as methyl or isopropyl; R$_2$ as hydrogen or ethyl; and the dotted triangular figure with oxygen at C(14,15) indicates that either a double bond or an epoxide is present.

5. A method according to claim 4, wherein said compound is R₁ as isopropyl; R₂ as hydrogen or ethyl; and the dotted triangular figure with oxygen at C(14,15) indicates that a double bond is present.

6. A method for protecting crops, trees, shrubs, stored grain and ornamentals from attack by insects, acarids and nematodes, said method comprising: applying to said crops, trees, shrubs, stored grain and ornamentals or to the locus in which they are grown or stored an insecticidally-effective amount of a compound represented by structural formula (I),

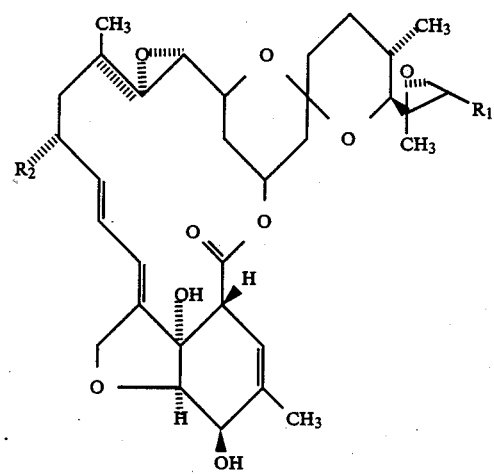

(I)

wherein said compound is R₁ as methyl or isopropyl; R₂ as hydrogen or ethyl; and the dotted triangular figure with oxygen at C(14,15) indicates that a double bond or an epoxide is present.

7. A method according to claim 6, wherein said compound is R₁ as isopropyl; R₂ as methyl; and the dotted triangular figure with oxygen at C(14,15) indicates that a double bond is present.

8. A method for the control of plant nematodes, said method comprising: applying to the foliage of plants, the soil in which they are grown or into the trunks thereof, a nematocidally-effective amount of a compound represented by structural formula (I),

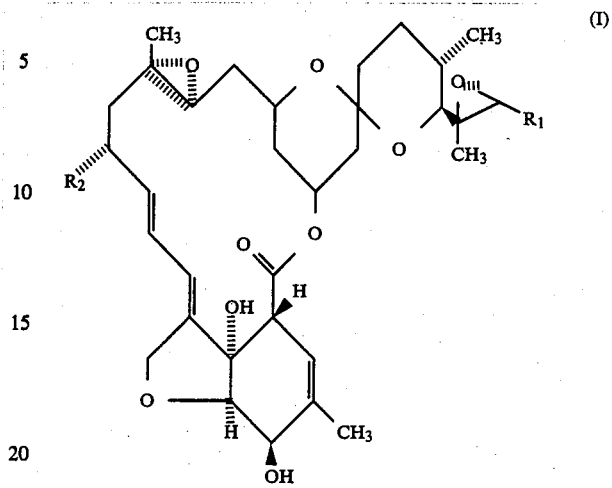

(I)

wherein said compound is R₁ as methyl or isopropyl; R₂ as hydrogen or ethyl; and the dotted triangular figure with oxygen at C(14,15) indicates that either a double bond or an epoxide is present.

9. A composition comprising: a prophylactically, therapeutically, pharmaceutically or insecticidally effective amount of a compound represented by structural formula (I),

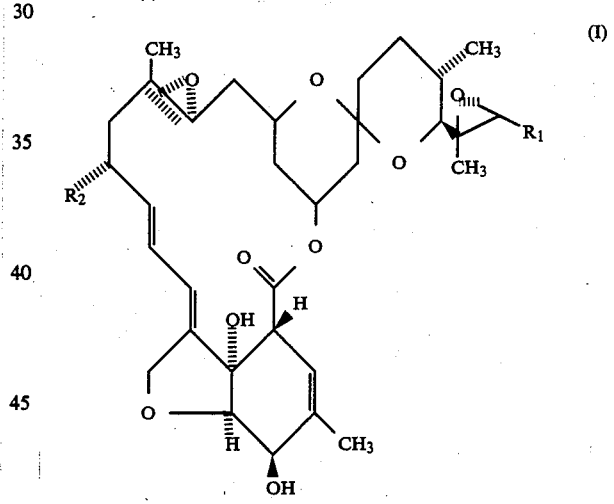

(I)

wherein R₁ is methyl or isopropyl; R₂ is hydrogen or ethyl; the dotted triangular figure with oxygen at C(14,15) indicates that either a double bond or an epoxide is present; and an inert carrier; wherein said composition is used to control endo- or ectoparasitic pests which infect warm-blooded animals or to control insect, acarid and nematode pests which infest agricultural crops.

* * * * *